United States Patent [19]

Porat et al.

[11] 4,443,896

[45] Apr. 24, 1984

[54] STERILIZED URINE SPECIMEN CONTAINER

[76] Inventors: Michael Porat, 52 Hamitnadev St., Affeka Tel-Aviv, Israel, 69690; Amir Porat, 18 Highland Dr., N. Caldwell, N.J. 07006

[21] Appl. No.: 534,110

[22] Filed: Sep. 20, 1983

Related U.S. Application Data

[63] Continuation of Ser. No. 362,556, Mar. 26, 1982, abandoned.

[30] Foreign Application Priority Data

Apr. 6, 1981 [IL] Israel .......................................... 62591

[51] Int. Cl.$^3$ ............................................. A47K 11/00
[52] U.S. Cl. ..................................... 4/144.1; 4/144.2; 4/144.4; 128/760; 215/10; 422/102
[58] Field of Search ................... 4/144.1, 144.2, 144.3, 4/144.4, 301, 661; 128/760; 215/10; 422/102

[56] References Cited

U.S. PATENT DOCUMENTS 4,211,749 7/1980 Kantner ................................ 215/10

*Primary Examiner*—Henry K. Artis
*Attorney, Agent, or Firm*—Dennison, Meserole, Pollack & Scheiner

[57] ABSTRACT

A urine specimen collecting unit including a cup and a separate lid selectivey sealed to the cup. The cup is of a generally conical configuration tapering from a closed base to a larger diameter open upper end. The lid includes a central depression received within the open end of an associated cup, a rim surrounding the depression for engagement with the upper edge of the cup, and a skirt depending peripherally from the rim below the depression and configured for locking engagement with the cup. The lid depression is configured to receive the closed base end of a superimposed cup. A tapered spout communicates through the rim and projects upwardly therefrom to lie adjacent the outer surface of a superimposed cup and within the confines of an imaginary cylinder surrounding the rim.

9 Claims, 3 Drawing Figures

U.S. Patent  Apr. 24, 1984  4,443,896
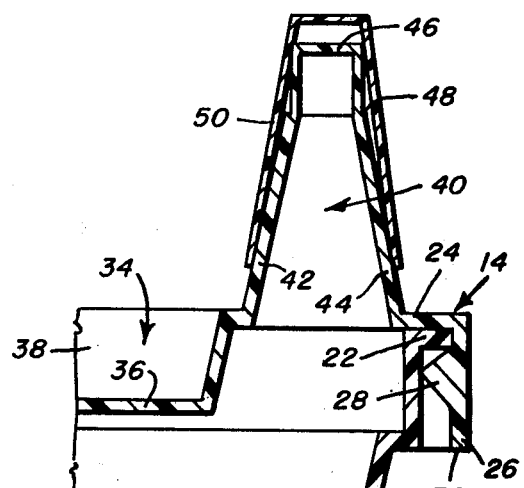
FIG. 2
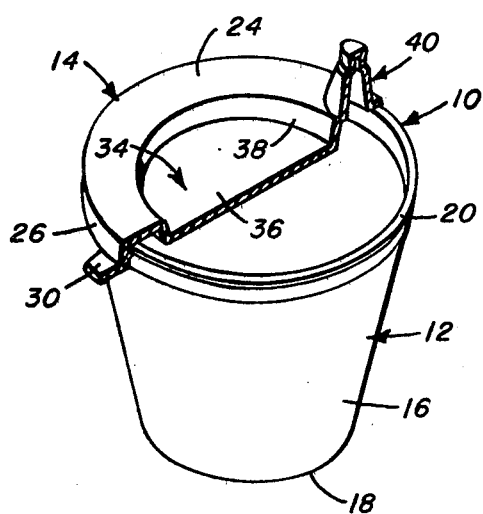
FIG. 1
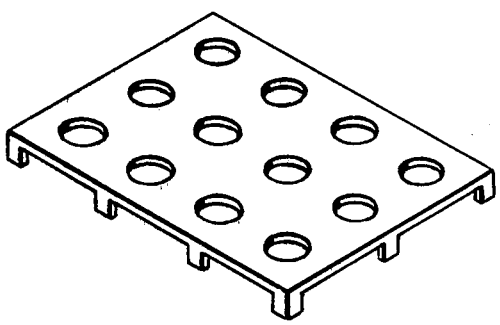
FIG. 3
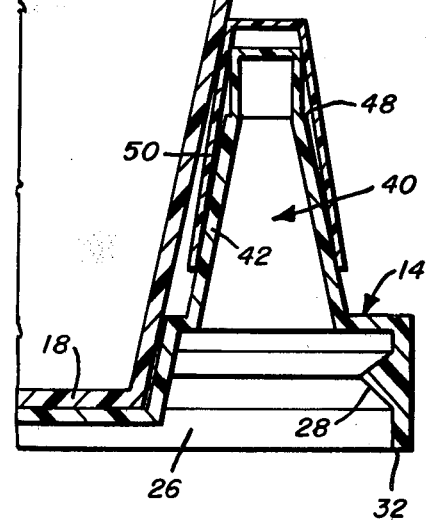

STERILIZED URINE SPECIMEN CONTAINER

CROSS-REFERENCE TO RELATED APPLICATION

This is a continuation of application Ser. No. 362,556, filed Mar. 26, 1982, now abandoned, for STERILIZED URINE SPECIMEN CONTAINER.

BACKGROUND OF THE INVENTION

The invention is concerned with sterilized urine specimen containers which are used to receive urine samples and contain the samples for transport to appropriate testing facilities whereat determinations are made as to the presence of bacteria, the quality of the urine, and the like.

While many procedures are known for the taking, preserving, transporting and dispensing of urine specimens, the most common procedure is to utilize a cup with a lid which is provided within a sealed bag with the entire unit sterilized.

When a urine sample is to be obtained, the sealed bag is opened, the lid removed from the cup, the patient cleansed with a napkin prepared with a cleaning material, and the urine deposited into the cup, after which the cup is again closed with the lid. The cup is then put on a tray and transported to the laboratory or testing facility. At the laboratory, the cup is opened and the contents poured into a petri dish or the like for testing purposes. It is also possible to test the urine chemically by introducing a testing strip into the cup. This strip can subsequently be computer analyzed.

The above described system has several disadvantages. For example, when initially opening the cup, the lid will normally be placed on some surface during the filling of the cup. This in turn gives rise to the possibility of contamination of the lid and subsequent contamination of the urine upon replacement of the lid. In an attempt to avoid this problem, provision is normally made for a pre-sterilized paper base upon which the lid can be placed.

Problems also arise with regard to the transport of the cups to the laboratory in that the conventional cups are normally loosely contained on a tray with little or no means for stabilizing the cups and preventing accidental opening thereof and possible damage to or contamination of the specimens.

Further problems arise in the laboratory itself in that it has previously been necessary to open the cup, by a removal of the lid itself, for a pouring out of the urine into the examination or testing plates. This in turn gives rise to the possibility of further contamination of the urine, possibly by bacteria on the edges of the cup or in the air of the laboratory, thus giving rise to inaccurate test results.

SUMMARY OF THE INVENTION

The invention detailed herein is specifically proposed to avoid the problems and disadvantages with the known systems through unique improvements in a cup and lid construction and relationship.

The cup is to be of a generally conical configuration tapering from a closed base end to a larger diameter open upper end. The lid includes a depending peripheral skirt which locks about and seals the open upper end of the cup. The lid, immediately inward of the skirt, includes an annular rim which in turn surrounds a central depression. The depth of the depression is less than that of the skirt whereby, upon the placing of the lid on a flat surface, only the lower edge of the skirt touches the surface, the depression being elevated relative thereto. In this manner, no portion of the lid which is exposed to the contents of the cup will normally come in contact with any surface. Thus, a source of substantial contamination is avoided. The depression has a slightly inclined peripheral wall and conforms to the base end portion of the cup whereby the lidded cups are specifically adapted for stable stacking.

Of particular significance is the provision of an integral spout rising from the rim and communicating with the interior of the lid, this in turn places the spout in direct communication with the interior of an associated cup. The spout is slightly transversely elongated and includes tapered side walls inwardly offset, respectively, from the depression wall and the lid skirt. The inner tapered wall of the skirt generally follows the taper of the wall of the depression and, being offset therefrom, lies adjacent the outer surface of a stacked cup without interference with the stacking thereof. The outer tapered wall of the spout, inwardly offset from the skirt, clearly positions the entire spout within the confines of an imaginary cylinder defined by the skirts of stacked lidded cups.

The upper end of the spout is sealed and selectively severable for a pouring of the contents of the cup, or otherwise providing access thereto. The severing of the upper portion of the spout is facilitated by a peripheral ledge or step. The spout is in turn provided with a cap or cover closely conforming thereto and, preferably at all times other than during the actual accessing of the urine through the spout, providing a seal therefor. In this manner, the upper portion of the spout, particularly those areas which are to be severed and through which the urine is to be accessed, either by pouring or the introduction of a test strip, are protected from possible contamination. The relatively thin nature of the cover, as well as the close conformance thereof to the spout, do not in any way detract from the stackability of the lidded cups. The particular configuration and orientation of the spout, as well as the relationship between the cups and lid depressions, provide a unique stackability for the containers and significantly contribute to a compact grouping of the containers on a support tray or the like.

As one means of transporting stacked containers, it is contemplated that the tray incorporate multiple openings configured to receive the lower portions of the tapered cups therethrough, thus providing a highly stable engagement of the lower cup of each stack with the superimposed cups engaged within depressions of the cups immediately therebelow.

Removal of the individual lids can be facilitated by the provision of a projecting tab at one point about the peripheral skirt of each lid.

Additional objects and advantages of the invention are considered to reside in the details of construction and manner of use of the invention as more fully hereinafter described and claimed.

BRIEF DESCRIPTION OF THE DRAWINGS

FIG. 1 is a perspective view of the specimen collecting unit, including both lid and cup, of the present invention;

FIG. 2 is an enlarged cross-sectional detail of the stacking arrangement; and

FIG. 3 is a perspective view of the carrying tray.

DESCRIPTION OF THE PREFERRED EMBODIMENT

Referring now more specifically to the drawings, reference numeral 10 is used to generally designate the urine specimen collecting unit of the present invention. This unit comprises a cup 12 and an associated lid 14.

The cup 12 may be formed of an appropriate plastic or synthetic resinous material, glass or paper, and is of a generally conical configuration with the wall 16 tapering smoothly from a closed base end 18 to a larger diameter open upper end 20. The upper end 20 is surrounded by a slight outwardly projecting locking bead or flange 22.

The lid 14 includes a relatively wide flat rim 24 surrounded by a depending peripheral skirt 26 which is adapted for snug reception about the open upper end portion of the cup 16. The skirt in turn includes an inwardly projecting bead 28 adapted to engage immediately below the cup bead 22 for a releasable interlocking of the lid to the cup with the under surface of the rim 24 seating directly on the upper end 20 of the cup. It is contemplated that the lid be of an appropriate plastic, such as polyethylene or polypropylene, incorporating a sufficient degree of resiliency so as to enable a snap mounting and removal of the lid. This mounting and removal of the lid can be facilitated by a laterally projecting tab 30 extending from the lower edge 32 of the skirt 26 at one point thereabout.

The lid 14 also includes a central depression 34 immediately inward of the rim 24 and defined by a flat bottom panel 36 and a tapered or inclined peripheral wall 38. The size and configuration of the depression 34, including the taper of the peripheral wall 38 thereof, conforms to the lower portion of the associated cup 12 whereby a stable stacking of the lid-closed cups is possible. The depth of the depression 34 is less than the height of the skirt 26. In this manner, the skirt 26 will maintain the bottom surface of the depression out of contact with a tabletop or the like on which the lid might be placed when removed from the cup.

Each lid 14 includes a spout 40 projecting upwardly from the rim 24 and communicating with the interior of the lid, and hence with the interior of an associated cup. The spout 40 is transversely elongated, so as to facilitate the introduction of testing paper strips, and the like, and includes opposed upwardly tapering sides 42 and 44. The side 42 is slightly inwardly offset relative to the depression wall 38 and tapers or inclines at approximately the same angle as that of the depression wall 38 to lie immediately outward of a stacked cup without interference with the stacking thereof. The spout wall 44 is inwardly offset from the outer edge of the rim 24 and the skirt 26 depending therefrom. This wall 44 is inclined at approximately the same angle as the inclination of the wall 42, providing a symmetrically configured spout lying entirely within the lateral confines of the rim 24 and hence within an imaginary cylinder surrounding the rims of stacked units. Such an imaginary cylinder can be considered to be defined by the vertically aligned skirts and will be apparent from the illustration of the stacked containers in FIG. 2. The upper end 46 of the spout is integrally formed therewith and sealed. When access through the spout is desired, either for a pouring of the contents of the cup or for the introduction of test devices, the upper portion of the spout is to be severed by appropriate sterile means, such as scissors. This severing of the upper portion of the spout 40 is facilitated by the provision of a ledge or step 48 upon which the severing implement can rest during the severing operation.

The spout 40 is in turn covered and protected by a removable cover or cap 50 which is tapered to closely conform to the spout for snug sealing reception thereover. This cap, while effectively sealing and protecting the spout, both before and subsequent to the opening thereof, mounts in a manner which in no way interferes with the stacking of the units. This is insured by the slight offsetting of the spout wall 42 from the peripheral walls 38 of the depression 34. It will be recognized that the cover 50 protects the sterilized spout prior to the severing thereof. In this manner, utilizing a sterile severing implement, contamination at the point of severing is avoided. The severed edge, being free of contamination, will not in turn contaminate the urine poured therethrough. A replacement of the cover 50 will insure the continued freedom from external contamination.

FIG. 3 illustrates a preferred form of carrying tray wherein circular apertures are provided which receive and stabilize the tapered cups. With a positive stabilization of the cups by the tray, and in light of the stacking capability of the units through the lid depressions, a positive transport of multiple filled containers is possible without the normally encountered danger of spillage or damage.

In use, the patient or nurse receives the unit, preferably sealed within a bag to maintain sterilization. The user opens the bag and removes the closed-lid cup. The lid is then removed and normally placed on a flat surface, at this point, it is significant that the skirt 26 is of a greater height than the depth of the depression 34. In this manner, the lid is solely supported on the lower edge 32 of the skirt 26 with the intermediate portion of the lid, including the depression 34, maintained out of contact with the supporting surface, a potential source of contamination. Urine is then introduced into the cup and the lid remounted. At that point, appropriate identifying information can be written on the lid and cup and the whole unit placed within the supporting tray, either directly within the cup receiving openings or stacked on previously placed cups. The cooperative relationship between the lower portion of each cup and the depression of a subjacent lid insures a proper stable stacking of the cups with the spouts positioned within the confines of the outermost limits of the cup lids to allow for a compact grouping of the units.

The tray supported units can then be transported to the laboratory or testing facility where, under appropriate conditions, within a clean area, and usually under a laminar flow of sterile air, the cover or cap 50 is removed and the spout of the lid severed, as by sterilized scissors or the like positioned by the shoulder or step 48. The urine specimen can then be poured from the spout into an appropriate testing dish or the like. Alternatively, a strip of test paper can be introduced into the elongated spout. It will be appreciated that the provision of the cover or cap 50 is significant in avoiding contamination to the spout on the outer surface in the area of severing which could otherwise contaminate the discharging urine or a test strip as it is being introduced. It will also be recognized that the sterility of the spout can be maintained by a remounting of the cap should it be desirable to retain a portion of the specimen within the container.

From the foregoing, it is to be appreciated that a unique specimen container has been defined. The container comprises a cup and lid combination which particularly adapts the container for the grouping and stacking of multiple containers, as well as for the maintenance of the sterility of the contents, both during storage and during subsequent dispensing or accessing of the contents for testing purposes. Significant advantages of the container or unit of the invention can be attributed to the construction and orientation of the lid spout and the relationship thereof to both the outer periphery of the lid and a centrally defined cup receiving depression.

We claim:

1. A urine specimen collecting unit including a cup and a separate lid selectively sealed to said cup, the cup being of a generally conical configuration tapering from a closed base end to a larger diameter open upper end, the lid comprising a central depression configured to receive the closed base end of the cup for a stacking of lid-closed cups, an annular rim surrounding said depression, a skirt depending peripherally from said rim for engaging about the open upper end of the cup upon a positioning of the lid thereover, said central depression being receivable centrally within the open upper end of the cup in inwardly spaced relation to the cup wall, and a spout communicating through said rim and projecting upwardly from said rim to lie adjacent the wall of a superimposed cup exteriorly thereof and within the confines of an imaginary cylinder surrounding said rim.

2. A urine specimen collecting unit as in claim 1, including a removeable cap receivable over said spout and closely conforming to the configuration thereof.

3. A urine specimen collecting unit as in claim 2, wherein said depending skirt depends below said central depression.

4. A uring specimen collecting unit as in claim 1, wherein said depression has a peripheral wall, said peripheral wall and said skirt defining said rim therebetween, said spout being inwardly positioned relative to both said peripheral wall and said skirt.

5. A urine specimen collecting unit as in claim 4, wherein the peripheral wall of the depression is outwardly inclined, said spout including opposed outwardly converging walls, one of said converging walls being inwardly spaced relative to the peripheral wall and at generally the same inclination thereof.

6. For use in conjunction with a cup having a sealed base end and an open upper end for defining a urine specimen collecting unit, a separate lid selectively sealable to said cup, the lid comprising a central depression configured to receive the closed base end of a cup for stacking, an annular rim surrounding said depression, a skirt depending peripherally from said rim for engaging about the open upper end of a cup upon a positioning of the lid thereover, said central depression being receivable centrally within the open upper end of a cup, and a spout communicating through said rim and projecting upwardly from said rim, said depression having a peripheral wall, said peripheral wall and said skirt defining said rim therebetween, said spout being inwardly positioned relative to both said peripheral wall and said skirt.

7. A urine specimen collecting unit lid as in claim 6, including a removeable cap receivable over said spout and closely conforming to the configuration thereof.

8. A urine specimen collecting unit lid as in claim 7, wherein said depending skirt depends below said central depression.

9. A urine specimen collecting unit lid as in claim 6, wherein the peripheral wall of the depression is outwardly inclined, said spout including opposed outwardly converging walls, one of said converging walls being inwardly spaced relative to the peripheral wall and at generally the same inclination thereof.

* * * * *